(12) United States Patent
Weber et al.

(10) Patent No.: US 8,043,358 B2
(45) Date of Patent: Oct. 25, 2011

(54) STENT WITH OVERLAP AND HIGH EXTENSION

(75) Inventors: Jan Weber, Maple Grove, MN (US);
Karl A. Jagger, Deephaven, MN (US);
James Anderson, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 389 days.

(21) Appl. No.: 11/392,047

(22) Filed: Mar. 29, 2006

(65) Prior Publication Data
US 2007/0239257 A1    Oct. 11, 2007

(51) Int. Cl.
*A61F 2/06*    (2006.01)
(52) U.S. Cl. .................................................. 623/1.15
(58) Field of Classification Search ................ 623/1.15, 623/1.16, 1.17, 1.35
See application file for complete search history.

(56) References Cited

U.S. PATENT DOCUMENTS

| | | | |
|---|---|---|---|
| 6,013,091 A | 7/1980 | Dahms | 83/150 |
| 4,994,071 A | 2/1991 | Gregor | 606/194 |
| 5,630,829 A | 5/1997 | Lauterjung | 606/198 |
| 5,755,774 A * | 5/1998 | Pinchuk | 623/1.13 |
| 5,755,776 A | 5/1998 | Al-Saadon | 623/1 |
| 5,776,161 A | 7/1998 | Globerman | 606/194 |
| 5,836,966 A | 11/1998 | St. Germain | |
| 5,876,449 A | 3/1999 | Starck et al. | 623/12 |
| 5,906,640 A | 5/1999 | Penn et al. | 623/1 |
| 5,922,021 A | 7/1999 | Jang | 623/1 |
| 6,017,363 A * | 1/2000 | Hojeibane | 623/23.7 |
| 6,030,414 A | 2/2000 | Taheri | 623/1 |
| 6,033,433 A | 3/2000 | Ehr | 623/1 |
| 6,048,361 A | 4/2000 | Von Oepen | 623/1 |
| 6,056,775 A | 5/2000 | Borghi | 623/1.16 |
| 6,113,627 A * | 9/2000 | Jang | 623/1.5 |
| 6,123,721 A | 9/2000 | Jang | 623/1 |
| 6,129,754 A | 10/2000 | Kanesaka | 623/1 |
| 6,193,747 B1 | 2/2001 | von Oepen | 623/1.15 |
| 6,200,334 B1 | 3/2001 | Jang | 623/1.1 |
| 6,210,429 B1 | 4/2001 | Vardi | 623/1.11 |
| 6,231,598 B1 | 5/2001 | Berry et al. | |
| 6,251,134 B1 | 6/2001 | Alt et al. | 623/1.16 |
| 6,258,116 B1 | 7/2001 | Hojeibane | 623/1.16 |
| 6,290,673 B1 | 9/2001 | Shanley | 604/102.02 |
| 6,325,826 B1 | 12/2001 | Vardi | 623/1.35 |
| 6,331,189 B1 * | 12/2001 | Wolinsky et al. | 623/1.15 |
| 6,334,870 B1 | 1/2002 | Ehr | 623/1.16 |
| 6,348,065 B1 | 2/2002 | Brown et al. | 623/1.16 |
| 6,361,555 B1 | 3/2002 | Wilson | 623/1.11 |
| 6,409,753 B1 | 6/2002 | Brown et al. | 623/1.15 |
| 6,432,132 B1 | 8/2002 | Cottone et al. | 623/1.15 |
| 6,436,134 B2 | 8/2002 | Richter | 623/1.15 |

(Continued)

FOREIGN PATENT DOCUMENTS

EP    1197189    4/2002

(Continued)

*Primary Examiner* — S. Thomas Hughes
*Assistant Examiner* — Jocelin Tanner
(74) *Attorney, Agent, or Firm* — Vidas, Arrett & Steinkraus, P.A.

(57) ABSTRACT

A stent may comprise a plurality of serpentine bands that overlap along the length of the stent. Each serpentine band may comprise a plurality of alternating first struts and second struts connected by a plurality of alternating proximal turns and distal turns. Each first strut defines a curvilinear path different from that of each second strut.

19 Claims, 8 Drawing Sheets

U.S. PATENT DOCUMENTS

| | | | | |
|---|---|---|---|---|
| 6,464,722 B2 | 10/2002 | Israel et al. | | 623/1.17 |
| 6,468,302 B2 | 10/2002 | Cox et al. | | 623/1.15 |
| 6,506,211 B1 | 1/2003 | Skubitz et al. | | |
| 6,565,598 B1 | 5/2003 | Lootz | | 623/1.15 |
| 6,579,309 B1 | 6/2003 | Loos | | 623/1.16 |
| 6,579,310 B1 | 6/2003 | Cox et al. | | 623/1.16 |
| 6,582,394 B1 | 6/2003 | Reiss | | 604/96 |
| 6,599,315 B2 | 7/2003 | Wilson | | 623/1.11 |
| 6,602,285 B1 | 8/2003 | Von Oepen et al. | | 623/1.17 |
| 6,663,664 B1* | 12/2003 | Pacetti | | 623/1.2 |
| 6,709,453 B2 | 3/2004 | Pinchasik et al. | | 623/1.15 |
| 6,730,116 B1* | 5/2004 | Wolinsky et al. | | 623/1.16 |
| 6,749,628 B1 | 6/2004 | Callol | | 623/1.15 |
| 6,821,292 B2 | 11/2004 | Pazienza et al. | | 623/1.15 |
| 6,835,203 B1 | 12/2004 | Vardi | | 623/1.16 |
| 7,220,275 B2* | 5/2007 | Davidson et al. | | 623/1.35 |
| 2001/0056297 A1 | 12/2001 | Hojeibane | | 623/1.16 |
| 2001/0056298 A1 | 12/2001 | Brown et al. | | 623/1.16 |
| 2002/0007212 A1 | 1/2002 | Brown et al. | | 623/1.16 |
| 2002/0035395 A1 | 3/2002 | Sugimoto | | |
| 2002/0042649 A1* | 4/2002 | Schaldach et al. | | 623/1.15 |
| 2002/0049487 A1* | 4/2002 | Lootz et al. | | 623/1.11 |
| 2002/0095208 A1 | 7/2002 | Gregorich et al. | | 623/1.15 |
| 2002/0151963 A1* | 10/2002 | Brown et al. | | 623/1.15 |
| 2002/0193873 A1 | 12/2002 | Brucker | | 623/1.11 |
| 2003/0045925 A1 | 3/2003 | Jayaraman | | |
| 2003/0195606 A1 | 10/2003 | Davidson | | 623/1.15 |
| 2003/0225449 A1 | 12/2003 | Denison | | |
| 2004/0073290 A1* | 4/2004 | Chouinard | | 623/1.15 |
| 2004/0138737 A1 | 7/2004 | Davidson | | 623/1.15 |
| 2004/0167609 A1 | 8/2004 | Majercak | | |
| 2004/0186551 A1* | 9/2004 | Kao et al. | | 623/1.15 |
| 2004/0267352 A1 | 12/2004 | Davidson | | 623/1.16 |
| 2004/0267353 A1 | 12/2004 | Gregorich | | 623/1.16 |
| 2005/0010278 A1 | 1/2005 | Vardi et al. | | 606/167 |
| 2005/0038501 A1 | 2/2005 | Moore, Jr. et al. | | |
| 2005/0060027 A1 | 3/2005 | Khenansho | | |
| 2005/0102023 A1 | 5/2005 | Yadin | | 623/1.16 |
| 2005/0131524 A1 | 6/2005 | Majercak et al. | | |
| 2005/0131526 A1 | 6/2005 | Wong | | |
| 2005/0154444 A1 | 7/2005 | Quadri et al. | | 623/1.23 |
| 2005/0228483 A1 | 10/2005 | Kaplan | | 623/1.11 |
| 2006/0173528 A1 | 8/2006 | Feld et al. | | |
| 2007/0208415 A1 | 9/2007 | Grotheim et al. | | |

FOREIGN PATENT DOCUMENTS

| | | |
|---|---|---|
| EP | 1707161 | 10/2006 |
| EP | 1707162 | 10/2006 |
| WO | 9965418 | 12/1999 |
| WO | 9965421 | 12/1999 |
| WO | 0003661 | 1/2000 |
| WO | 0187372 | 11/2001 |
| WO | 2004/019820 | 3/2004 |
| WO | 2005/009295 | 2/2005 |

* cited by examiner

STENT WITH OVERLAP AND HIGH EXTENSION

CROSS-REFERENCE TO RELATED APPLICATIONS

Not Applicable

STATEMENT REGARDING FEDERALLY SPONSORED RESEARCH

Not Applicable

FIELD OF THE INVENTION

This invention relates to implantable medical devices, such as stents, their manufacture, delivery and methods of use.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs capable of providing scaffolding support to a vessel bifurcation.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent having a proximal end and a distal end, the stent comprising a tubular body defined by a plurality of serpentine bands. Each serpentine band comprises a plurality of interconnected proximal turns and distal turns. Each proximal turn is longitudinally and circumferentially offset from each distal turn. Every proximal turn is connected to a first distal turn by a first strut and to a second distal turn by a second strut. Each first strut defines a curvilinear path different than that of each second strut. Each first strut and each second strut further comprises a peak and a valley. The peak of each strut is closer to the connected distal turn than to the connected proximal turn, and the valley of each strut is closer to the connected proximal turn than to the connected distal turn. All peaks of a serpentine band are substantially aligned along a first stent circumference, and all valleys of a serpentine band are substantially aligned along a second stent circumference.

In at least one other embodiment, a non-helical stent comprises a plurality of interconnected serpentine bands including a first serpentine band and a second serpentine band. Each serpentine band comprises a plurality of alternating proximal turns and distal turns connected by struts. The first serpentine band and the second serpentine band overlap such that a common circumference of the stent contacts each strut of the first serpentine band and each strut of the second serpentine band.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
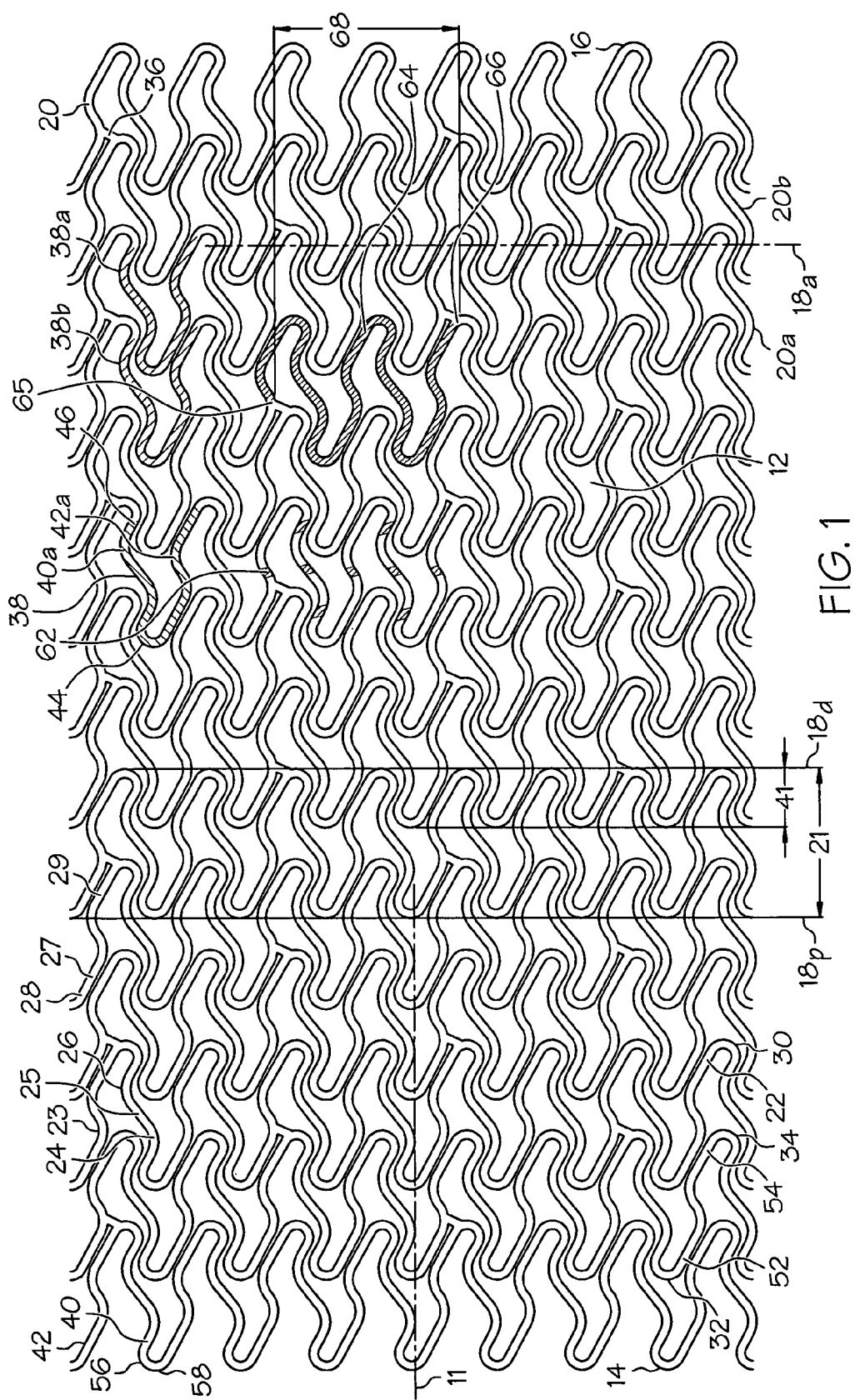
FIG. 1 shows a flat pattern for an embodiment of a stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated. Elements depicted in one figure may be combined with, and/or substituted for, elements depicted in another figure as desired.

Figure 2:
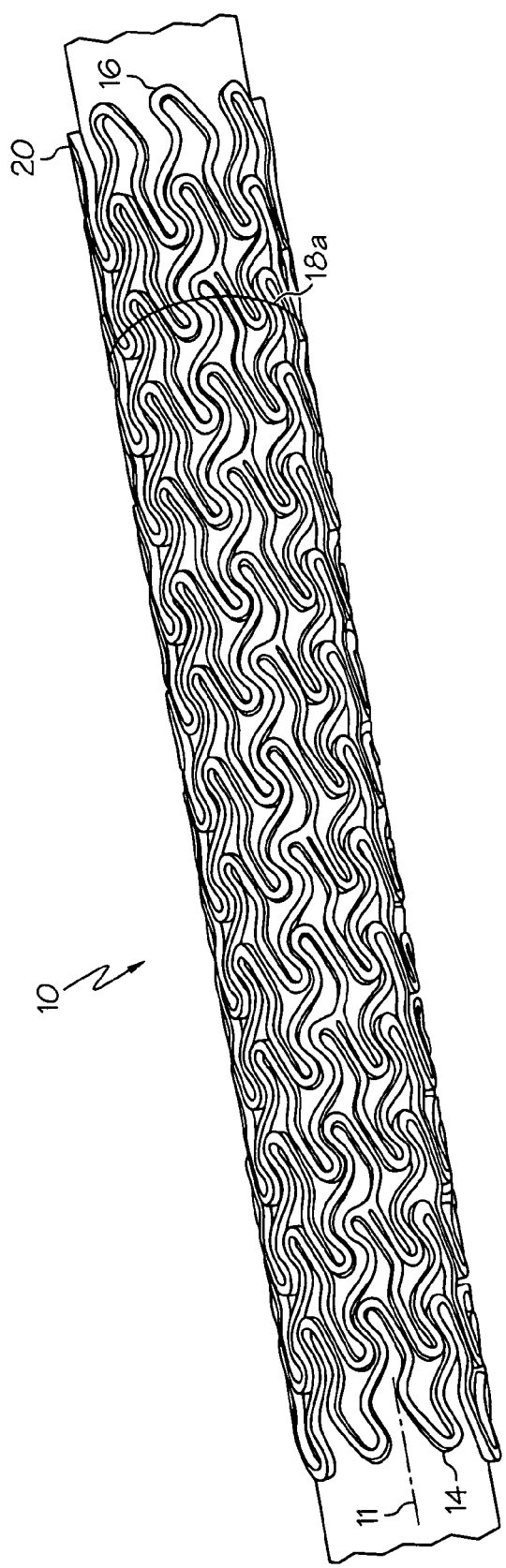
FIG. 2 shows an embodiment of a stent in a substantially unexpanded state.

FIG. 1 shows a flat pattern for an embodiment of a stent 10. FIG. 2 shows a stent 10 according to the pattern depicted in FIG. 1. The stent 10 has a proximal end 14 and a distal end 16, and comprises a plurality of structural elements that define a generally tubular body having a plurality of cells 12. The structural elements further define a plurality of interconnected serpentine bands 20. Adjacent serpentine bands 20 are connected by at least one connector 36.

Each serpentine band 20 comprises a plurality of struts 22 connected by turns 30. Turns 30 may comprise proximal turns 32, located on the proximal side of the serpentine band 20, or may comprise distal turns 34, located on the distal side of the serpentine band 20. Each strut 22 comprises a proximal end 52 that is connected to a proximal turn 32 and a distal end 54 that is connected to a distal turn 54.

Each strut 22 further comprises a curvilinear path between its proximal end 52 and distal end 54, and thus includes at least one bend 23. In some embodiments, a strut 22 may comprise multiple bends 23, such as a peak 24 and a valley 26, which may have different orientations. If a peak 24 may be considered convex from a given reference frame, a valley 26 may be considered concave. An inflection point 25 may be located along the curvilinear path between a peak 24 and a valley 26.

A valley 26 of a strut 22 may be located closer to the proximal turn 32 to which the strut 22 connects than to the distal turn 34 to which the strut 22 connects. A peak 24 of a strut 22 may be located closer to the distal turn 34 to which the strut 22 connects than to the proximal turn 32 to which the strut 22 connects.

Each strut 22 may further comprise straight portions 27. A straight portion 27 may comprise a proximal straight portion 28 or a distal straight portion 29. A proximal straight portion 28 may be located between the proximal end 52 of the strut 22 and a valley 26. A distal straight portion 29 may be located between a peak 24 and the distal end 54 of the strut 22.

Struts 22 may comprise first struts 40 or second struts 42. First struts 40 may alternate with second struts 42 about a serpentine band 20. Each turn 30 may connect at one end to a first strut 40 and may connect at the other end to a second strut 42. Each turn 30 may further comprise an upper portion 56 and a lower portion 56. It should be understood that "upper" and "lower" as used in this reference frame are relative terms that apply when used in conjunction with a flat pattern stent drawing, and a person of ordinary skill in the art would understand that the relative orientations may change when applied to a three dimensional stent framework of another reference frame.

In some embodiments, a proximal turn 32 upper portion 56 may connect to the proximal end 52 of a first strut 40. A proximal turn 32 lower portion 58 may connect to the proximal end 52 of a second strut 42. A distal turn 34 upper portion 56 may connect to the distal end 54 of a second strut 42. A distal turn 34 lower portion 58 may connect to the distal end 54 of a first strut 40.

All first struts 40 define a similarly shaped curvilinear path. All second struts 42 define a similarly shaped curvilinear path. The curvilinear path defined by the first struts 40 is different from the curvilinear path defined by the second struts 42. A peak 24 and a valley 26 of a second strut 42 may be located closer to one another than a peak 24 and a valley 26 of a first strut 40. The straight portion(s) 27 of a second strut 42 may be longer than the straight portion(s) 27 of a first strut 40. The proximal end 52 of a first strut 40 may be longitudinally and circumferentially offset from the distal end 54, wherein the distal end 54 may be located "above" the proximal end 52 (as depicted in FIG. 1), and the circumferential component of the offset may be oriented in a first direction. The proximal end 52 of a second strut 42 may be longitudinally and circumferentially offset from the distal end 54, wherein the distal end 54 may be located "below" the proximal end 52 (as depicted in FIG. 1), and the circumferential component of the offset may be oriented in a second direction.

The proximal straight portion 28 and the distal straight portion 29 of a first strut 40 may be substantially parallel. A straight portion 27 of a first strut 40 may be parallel to straight portions of other first struts 40, including other first struts 40 included within a common serpentine band 20 and other first struts 40 from different serpentine bands 20. Similarly, the proximal straight portion 28 and the distal straight portion 29 of a second strut 42 may be substantially parallel. A straight portion 27 of a second strut 42 may be parallel to straight portions of other second struts 42, including other second struts 42 included within a common serpentine band 20 and other second struts 42 from different serpentine bands 20. Further, straight portions 27 of first struts 40 may be parallel to straight portions 27 of second struts 42.

All proximal turns 32 included in a serpentine band 20 may be aligned about a common stent circumference 18$p$. All distal turns 34 included in a serpentine band 20 may be aligned about another common stent circumference 18$d$. Stent circumferences are intended to be oriented orthogonally to a stent central longitudinal axis 11.

All of the peaks 24 of all of the struts 22 of a serpentine band 20 may be substantially aligned along a stent circumference 18$p$. The peaks 24 of a serpentine band 20 may further be substantially aligned with the proximal turns 34 of an adjacent serpentine band 20 along a stent circumference 18$p$. All of the valleys 26 of all of the struts 22 of a serpentine band 20 may be substantially aligned along a stent circumference 18$d$. The valleys 26 of a serpentine band 20 may further be substantially aligned with the distal turns 34 of an adjacent serpentine band 20 along a stent circumference 18$d$.

Serpentine bands 20 are oriented such that adjacent serpentine bands 20 overlap one another along the length of the stent 10. Thus, a single common stent circumference 18$a$ may intersect a first serpentine band 20$a$ and a second serpentine band 20$b$. In some embodiments, there may be enough overlap that the common stent circumference 18$a$ intersects every strut 22 of the first serpentine band 20$a$ and every strut 22 of the second serpentine band 20$b$. Distal turns 34 of the first serpentine band 20$a$ may be located distal to the common stent circumference 18a, and proximal turns 32 of the second serpentine band 20b may be located proximal to the common stent circumference 18a.

The valleys 26 of struts 22 of a serpentine band 20 may be substantially aligned with the distal turns 34 of an adjacent serpentine band 20 about a stent circumference 18. The peaks 24 of struts 22 of a serpentine band 20 may be substantially aligned with the proximal turns 32 of an adjacent serpentine band 20 about a stent circumference 18.

Each serpentine band 20 may span a band length 21 as measured in a direction parallel to the stent central longitudinal axis 11. Adjacent serpentine bands 20 that overlap may define an overlap length 41 as measured in a direction parallel to the stent central longitudinal axis 11. Various embodiments of a stent 10 may include various amounts of overlap length 41. In some embodiments, the overlap length 41 may be 10%; 15%; 20%; 25%; 30%; 35% or greater than 35% of the band length 21.

Stents 10 made according to the pattern of FIG. 1 are intended to be considered non-helical type stents. The overlap described between adjacent serpentine bands 20 is true when the serpentine bands 20 have a purely circumferential orientation, wherein a circumference of the serpentine band 20 comprises an actual circumference of the stent 10, wherein the actual circumference is oriented orthogonal to the central longitudinal axis 11 of the stent 10.

Each serpentine band 20 may define a plurality of strut pairs 38. A strut pair 38 comprises a first strut 40a and an adjacent second strut 40b that are connected by a turn 30. Thus, a strut pair 38 includes a connected end 44 and an unconnected end 46. In some strut pairs 38, the connected turn 30 may comprise a proximal turn 32. In some strut pairs 38, the connected turn 30 may comprise a distal turn 34.

A portion of a first strut pair 38a of one serpentine band 20 may be nested within a portion of another strut pair 38b of an adjacent serpentine band 20. The connected end 44 of the first strut pair 38a may be nested between the struts 22 of the other strut pair 38b at its unconnected end 46. The overlap or nested area may span from the connected turn 30 to the valleys 26 of the struts 22 of the first strut pair 38a, and may span from the unconnected end 46 to the peaks 24 of the struts 22 of the other strut pair 38b.

Adjacent serpentine bands 20 are connected by at least one connector 36. A connector 36 may span from any suitable location of one serpentine band 20 to any suitable location of another serpentine band 20. In some embodiments, a connector 36 may connect to a turn 30. In some embodiments, a connector 36 may connect to a portion of a strut 22.

The embodiment of a stent 10 shown in FIG. 1 includes connectors 36 that span from a turn 36 of one serpentine band 20 to a strut 22 of an adjacent serpentine band 20. More specifically, connectors 36 span from a distal turn 34 upper portion 56 of one serpentine band 20 to a valley 26 of a strut 22 of an adjacent serpentine band 20.

Connectors 36 may have any suitable size and shape. In some embodiments, the connectors 36 may be considered short when compared to interconnecting elements of prior art stents. In some embodiments, the width of a connector 36 is the same width as other stent elements, such as turns 30 and struts 22. In some embodiments, the width of a connector 36 may be greater than its length.

A serpentine band 20 may define a free strut length 64 between points of connection to other portions of the stent 10, such as a first connection point 65 and a second connection point 66. In some embodiments, connection points 65, 66 are locations where the serpentine band 20 connects to a connector 36. In some embodiments, a first connection point 65 comprises a connection to stent structure located proximal to the serpentine band 20 along the length of the stent 10, and a second connection point 66 comprises a connection to stent structure located distal to the serpentine band 20 along the length of the stent 10. A free strut length 64 may comprise a plurality of struts 22 and a plurality of turns 30, and in some embodiments, may comprise four turns 30 and at least four struts 22. A free strut length 64 may also be described as being an unsupported length of a serpentine band 20 or an unconnected length of a serpentine band 20.

In some embodiments, the total distance traversed along a free strut length 64 between connection points 65, 66 is equal to or greater than a circumference 18 of the stent 10. In various embodiments, this may be true when the stent is in a nominal (i.e. as manufactured or as laser cut) state of expansion and/or when the stent is in a crimped or delivery state of expansion.

The free strut length 64 defines a circumferential length component 68, or distance between connection points 65, 66 as measured in a circumferential direction. A ratio of 'free strut length:circumferential length component' may be described for various free strut lengths 64. In various embodiments, the ratio may be 1:1, 2:1, 7:3, 3:1, 4:1, 5:1 or greater. For the highlighted free strut length 64 depicted in FIG. 1, the ratio is intended to be approximately 4.67:1. For the purposes of measuring free strut length 64 and circumferential length components 68, FIG. 1 may be considered a scale drawing for some embodiments of a stent 10.

A free strut length 64 defines a plurality of inflection zones 62, each inflection zone 62 containing an inflection point 25 wherein the concavity of the serpentine band 20 changes. A free strut length 64 may include any suitable number of inflection zones 62 and in some embodiments may include 5, 7 or 9 or more inflection zones 64. For example, nine inflection zones 62 are marked on an embodiment of a free strut length 64 in FIG. 1.

FIG. 2 shows a stent 10 formed in accordance with the pattern shown in FIG. 1 in a crimped or delivery state. The stent 10 is capable of a high amount of expansion.

Figure 3:
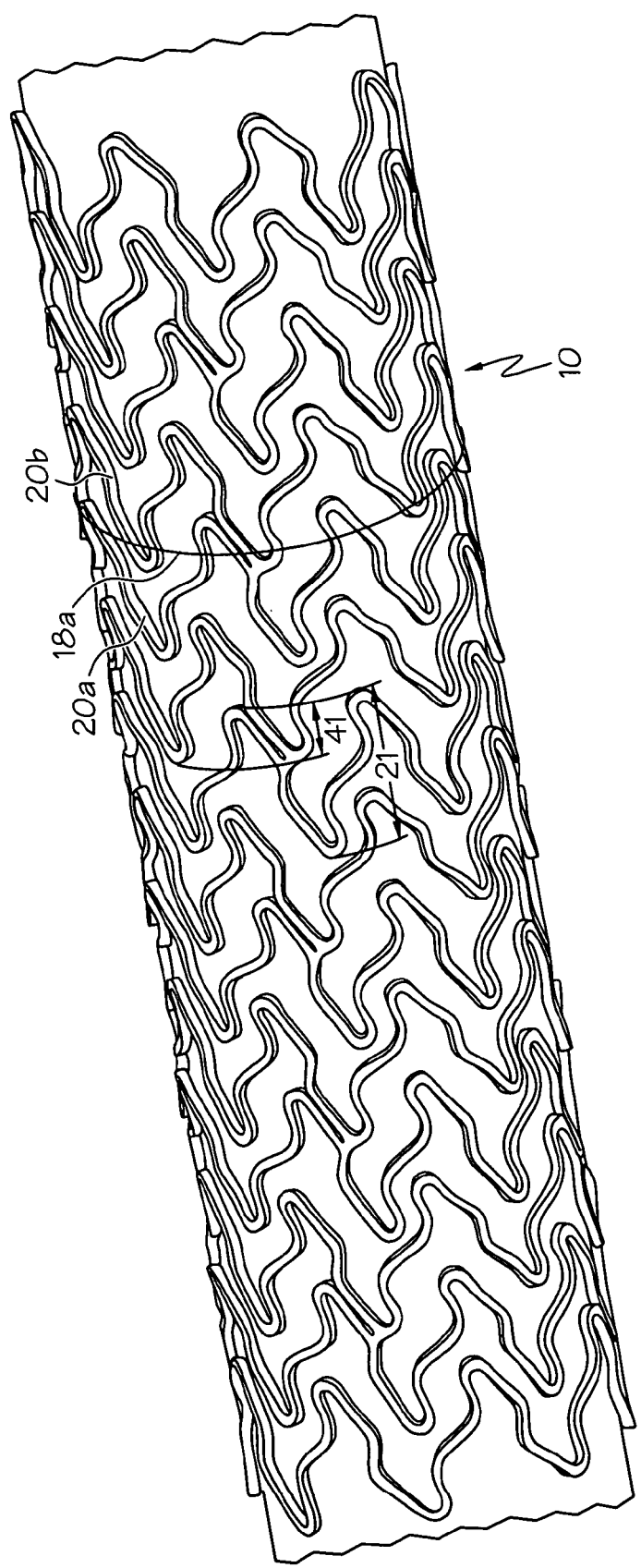
FIG. 3 shows the stent of FIG. 2 in a first state of expansion.

FIG. 3 shows the stent 10 of FIG. 2 in a first expanded state. The diameter of the stent 10 in the first expanded state is approximately 1.9 times the diameter of the stent 10 in the delivery state. Adjacent serpentine bands 20 continue to overlap along the length of the stent 10. A single common stent circumference 18a may continue to intersect a first serpentine band 20a and an adjacent second serpentine band 20b. In some embodiments, there may be enough overlap that the common stent circumference 18a intersects every strut 22 of the first serpentine band 20a and every strut 22 of the second serpentine band 20b.

Figure 4:
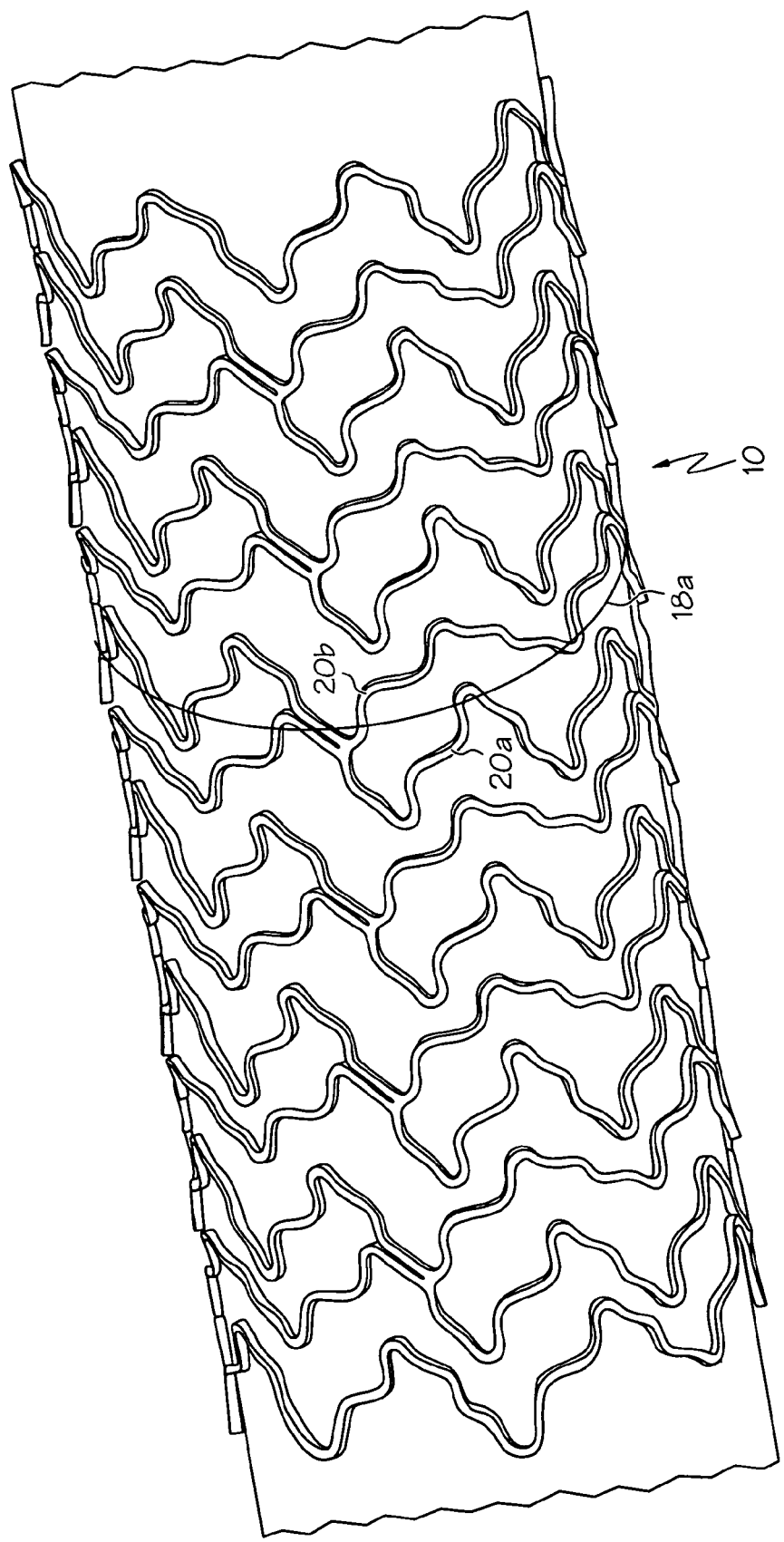
FIG. 4 shows the stent of FIG. 2 in a second state of expansion that is greater than the first state of expansion as shown in FIG. 3.

FIG. 4 shows the stent 10 of FIG. 2 in a second expanded state that is larger than the first expanded state. The diameter of the stent 10 in the second expanded state is approximately 2.7 times the diameter of the stent 10 in the delivery state. Even in the second expanded state, a single common stent circumference 18a may continue to intersect a first serpentine band 20a and an adjacent second serpentine band 20b.

The stent 10 is capable of being expanded far beyond the second expanded state depicted in FIG. 4. A ratio of 'crimped diameter:expanded diameter' is as high as 1:5.1 or greater for some embodiments of the stent 10, with the stent 10 maintaining proper shape and functionality, and the capability of providing adequate scaffolding support to a vessel wall. Thus, the expansion ratios are true without the stent becoming 'over-expanded.' It should be noted that the stents 10 described herein are capable of such expansion with a related axial foreshortening of 10% or less. Further, the stent diameters referred to may generally be considered outer diameters of the stent (i.e. crimped outer diameter:expanded outer diameter), however, in some embodiments, statements made herein may describe the inner diameters (i.e. crimped inner diameter:expanded inner diameter).

The stent 10 is further capable of varying degrees of expansion magnitude along its length. For example, a first portion of the stent 10 may be expanded in accordance with FIG. 4, while a second portion of the stent 10 may be expanded to an even greater degree. The first portion and the second portion may be immediately adjacent to one another along the length of the stent 10. Thus, the stent 10 is particularly useful at a vessel bifurcation.

Figure 5:
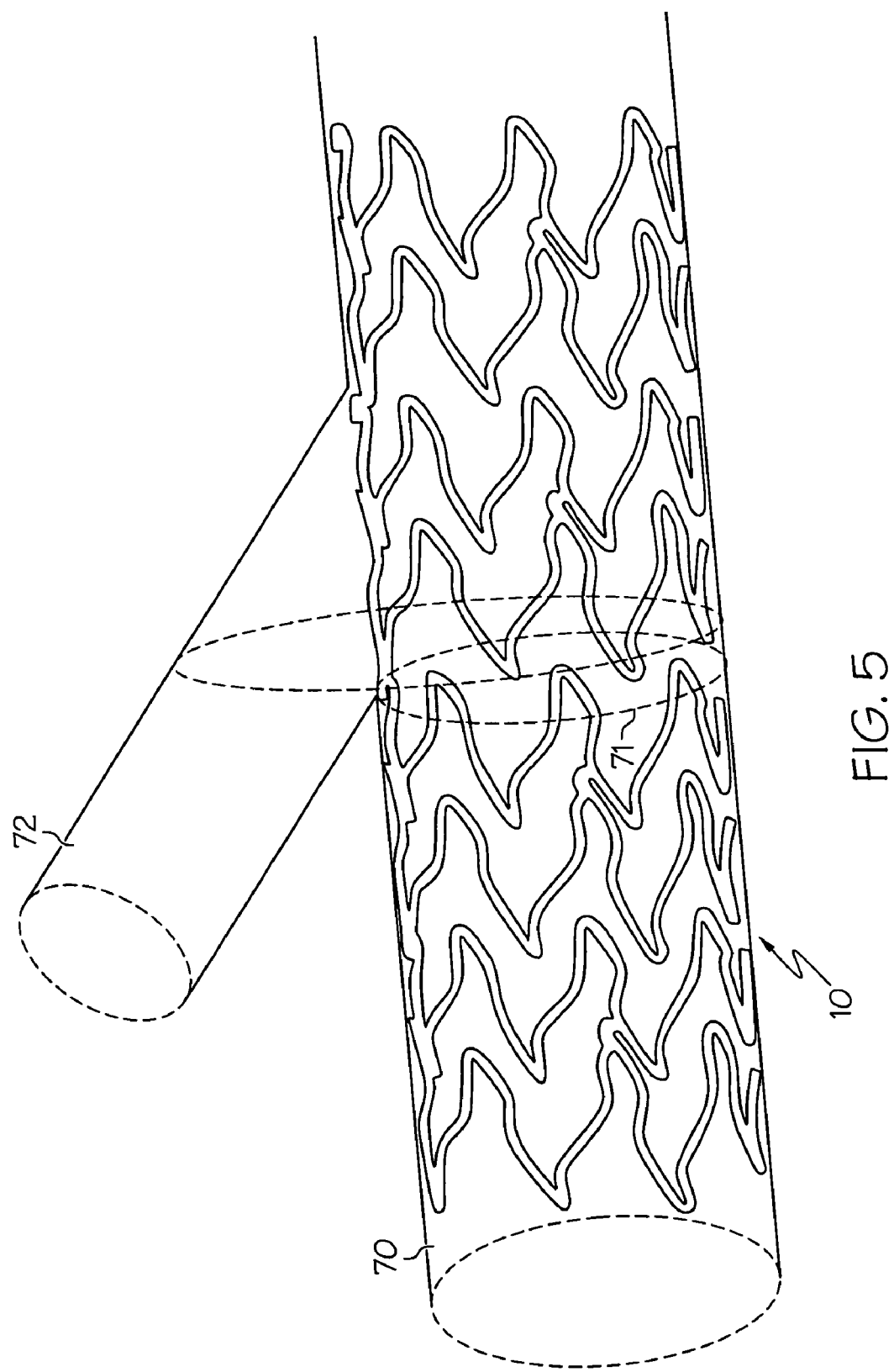
FIG. 5 shows an embodiment of a stent expanded in a vessel.

FIG. 5 shows an embodiment of a stent 10 oriented within a main vessel 70 near a bifurcation. The stent 10 is in a state of expansion roughly equivalent to the second expanded state, for example as shown in FIG. 4. The diameter/size of the stent 10 is approximately equivalent to the diameter/size 71 of the main vessel 70.

Figure 6:
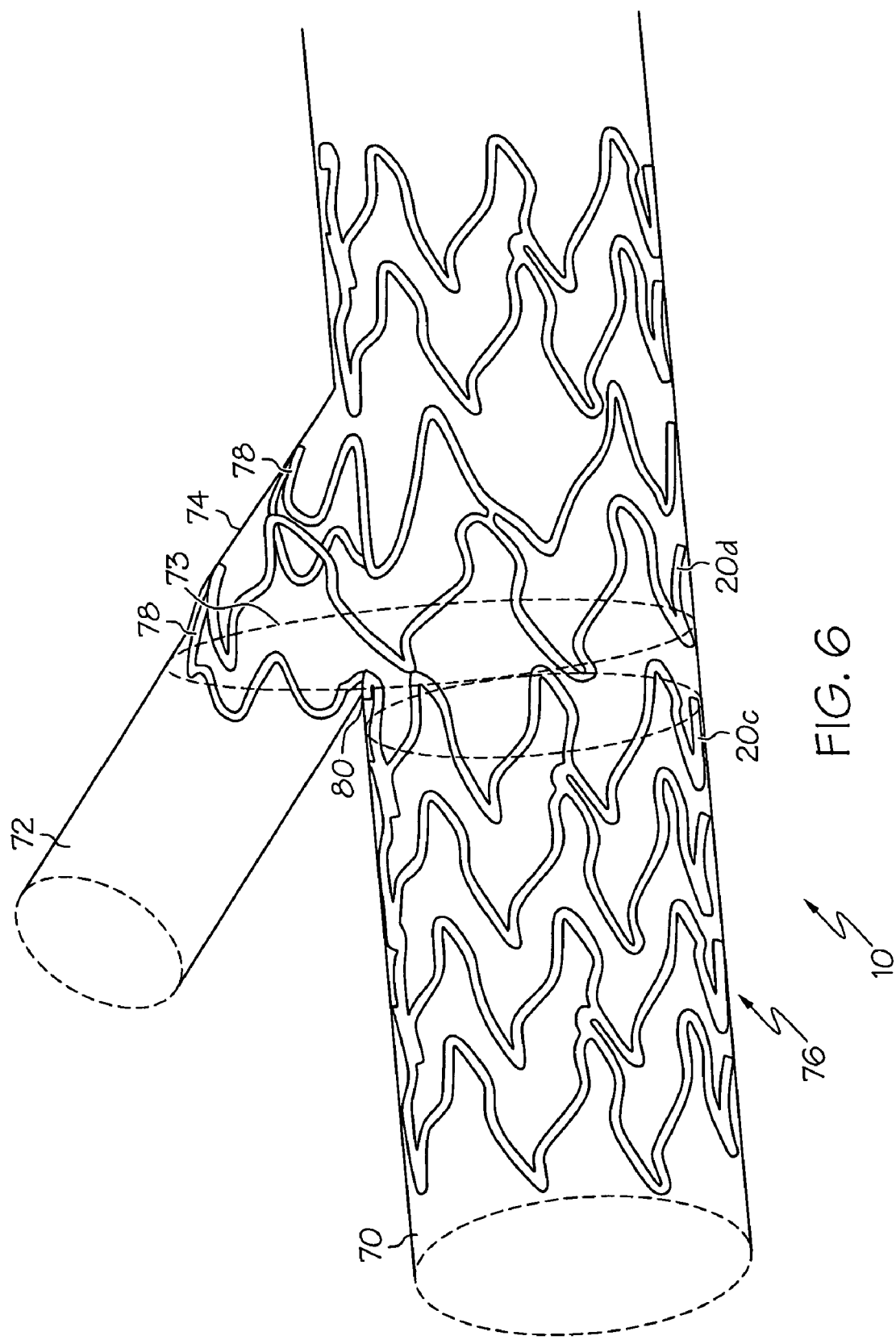
FIG. 6 shows the stent of FIG. 5, wherein a portion of the stent is further expanded into a bifurcation vessel.

The stent 10 includes structure that may be expanded into the side branch vessel 72 to support the side branch vessel 72, for example as shown in FIG. 6. The appropriate structure may be expanded, for example, using a balloon having first and second inflatable portions. The first inflatable portion may be used to expand the main cylindrical framework of the stent 10. The second inflatable portion, which may be inflatable separately from the first inflatable portion, may be used to expand a portion of the stent structure into the side branch vessel 72.

In some embodiments (not shown), a stent 10 may be provided with a side branch opening which may receive a second stent. The stent 10 may be positioned within a main vessel 70 with the side branch opening positioned in proximity to the side branch vessel 72. A second stent may be positioned within the side branch vessel 72 and engaged with the main stent 10.

FIG. 6 shows the stent 10 of FIG. 5, wherein a first portion 76 of the stent 10 remains in the first expanded state and a second portion 78 has been further expanded into the side branch vessel 72. Stent structure extending into the side branch vessel 72 provides support to the contralateral ostial wall 74. The stent 10, in the area of the second portion 78, is expanded to a size 73 greater than that of the main vessel 70. Thus, a first serpentine band 20c may be expanded to a first expanded state in a main vessel 70, and a second serpentine band 20d may be expanded partially into a side branch vessel 72 to a second, larger expanded state, wherein the first serpentine band 20c and the second serpentine band 20d may be immediately adjacent to one another along the length of the stent. A substantial portion of the first serpentine band 20c may be located to one side of the carina 80, while a substantial portion of the second serpentine band 20d may be located to the other side of the carina 80.

Any suitable portion of any serpentine band 20 may be expanded into a side branch vessel 72. Therefore, unlike prior art stents having a specific and dedicated side branch structure, the inventive stents 10 are not required to be placed with any specific rotational orientation with respect to the side branch vessel 72. The stents 10 may simply be placed according to a proper lengthwise orientation, and the serpentine band 20 portions that are consequently oriented with proximity to the side branch vessel 72 may be expanded into the side branch vessel 72.

Figure 7:
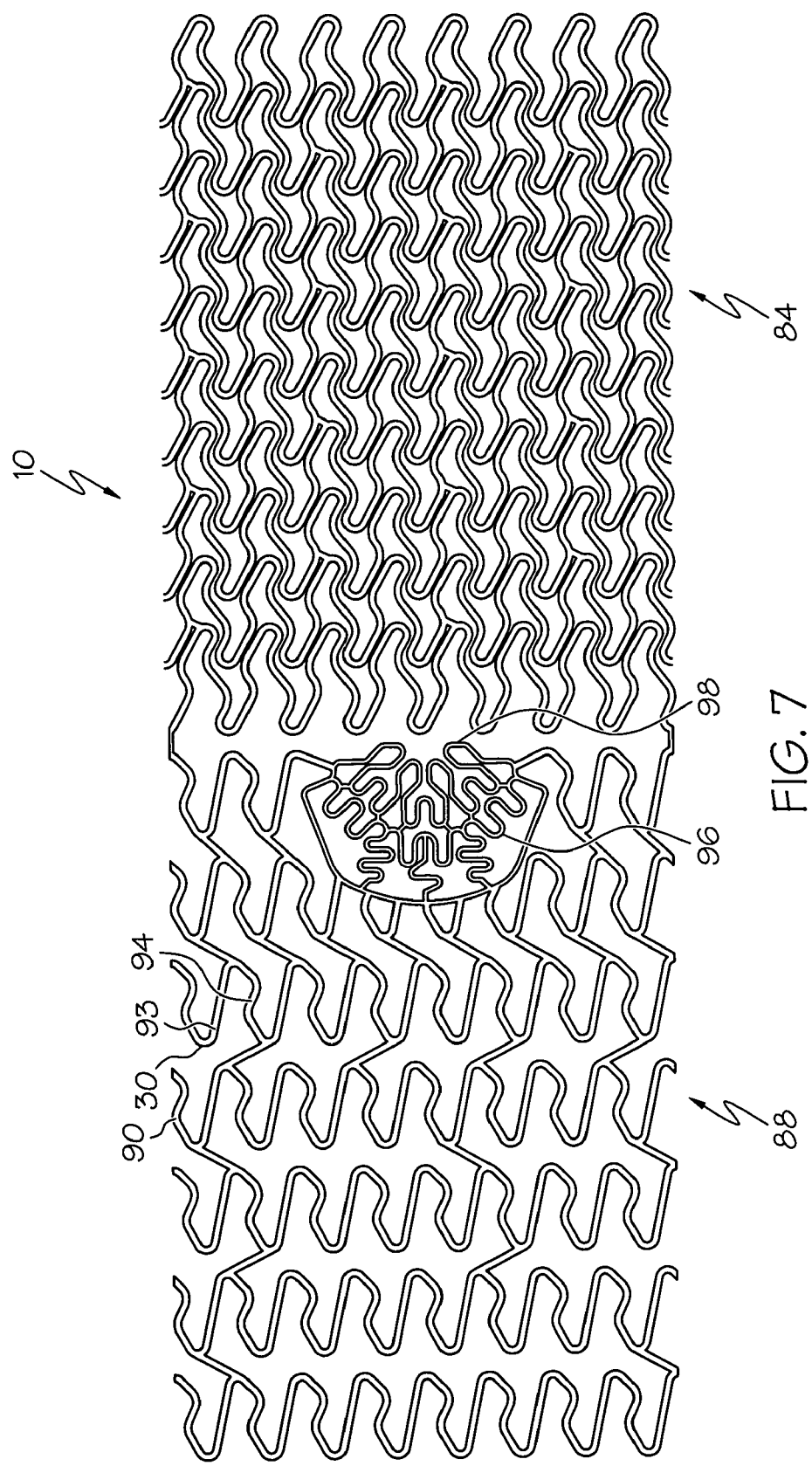
FIG. 7 shows a flat pattern for another embodiment of a stent.

In some instances, a dedicated side branch structure may be desirable. FIG. 7 shows a flat pattern for an embodiment of a stent 10 comprising a first portion 84 and a second portion 88. The first portion 84 may comprise overlapping serpentine bands 20 and stent structure as described herein, for example with respect to FIG. 1. The second portion 88 may comprise any suitable stent structure and a partial side branch structure 96.

The stent structure of the second portion 88 may comprise a pattern of serpentine bands 90 and connector struts 92. The serpentine bands 90 may comprise alternating straight struts 93 and s-shaped struts 94 connected by turns 30, for example as described with respect to various stent embodiments disclosed in U.S. patent application Ser. No. 11/262,692, the entire disclosure of which is hereby incorporated herein by reference in its entirety.

The partial side branch structure 96 may comprise any suitable stent side branch structure and in some embodiments may comprise a plurality of outwardly deployable petal structures 98. Examples of stent side branch structure are described, for example, in US Patent Application Publication No. 20050060027, the entire disclosure of which is hereby incorporated herein by reference in its entirety.

The partial side branch structure 96 may be considered a "partial" structure because it is not intended to support a full 360 degrees of the side branch vessel, and thus, the partial side branch structure 96 is reduced from the "full" side branch structures generally shown in the prior art. As depicted in FIG. 7, the partial side branch structure 96 extends approximately 180 degrees, and may thus be considered a half-crown structure.

When the stent 10 of FIG. 7 is expanded at a vessel bifurcation, the first portion 84 may extend into a side branch vessel 72 and support the contralateral ostial wall 74 (see FIG. 6). The partial side branch structure 96 may unfold into the side branch vessel 72 in proximity to the carina 80. Therefore, the first portion 84 of the stent 10 supports a first portion of the side branch vessel 72, and the partial side branch structure 96 supports a second portion of the side branch vessel 72, with each portion 84, 96 providing approximately half of the total support provided to the side branch vessel 72. Thus, a ratio of first portion 84 support to partial side branch structure 96 support is approximately 50:50. Various embodiments of stents 10 may include any suitable division between the amount of support provided to the side branch vessel 72 by each portion 84, 96. For example, various embodiments of stents 10 may have support ratios of 55:45, 60:40, 65:35, 70:30, etc., as well as 45:55, 40:60, 35:65, 30:70, etc.

In various embodiments of a stent 10, the stent pattern of the first portion 84 may comprise more of the total stent structure or less of the total stent structure than depicted in FIG. 7. For example, in some embodiments, the first portion 84 may comprise two or three serpentine bands 20 being located immediately adjacent to the partial side branch structure 96. Desirably, the stent axial length spanned by the first portion 84 is equal to or greater than the stent axial length spanned by the partial side branch structure 96. In some embodiments, a stent 10 may include the structure of the second portion 88 on both proximal and distal sides of the first portion 84. Further, the pairing of the partial side branch structure 96 and the first portion 88 may be located anywhere along the length of the stent 10, and in some embodiments is substantially centered as shown in FIG. 7.

Figure 8:
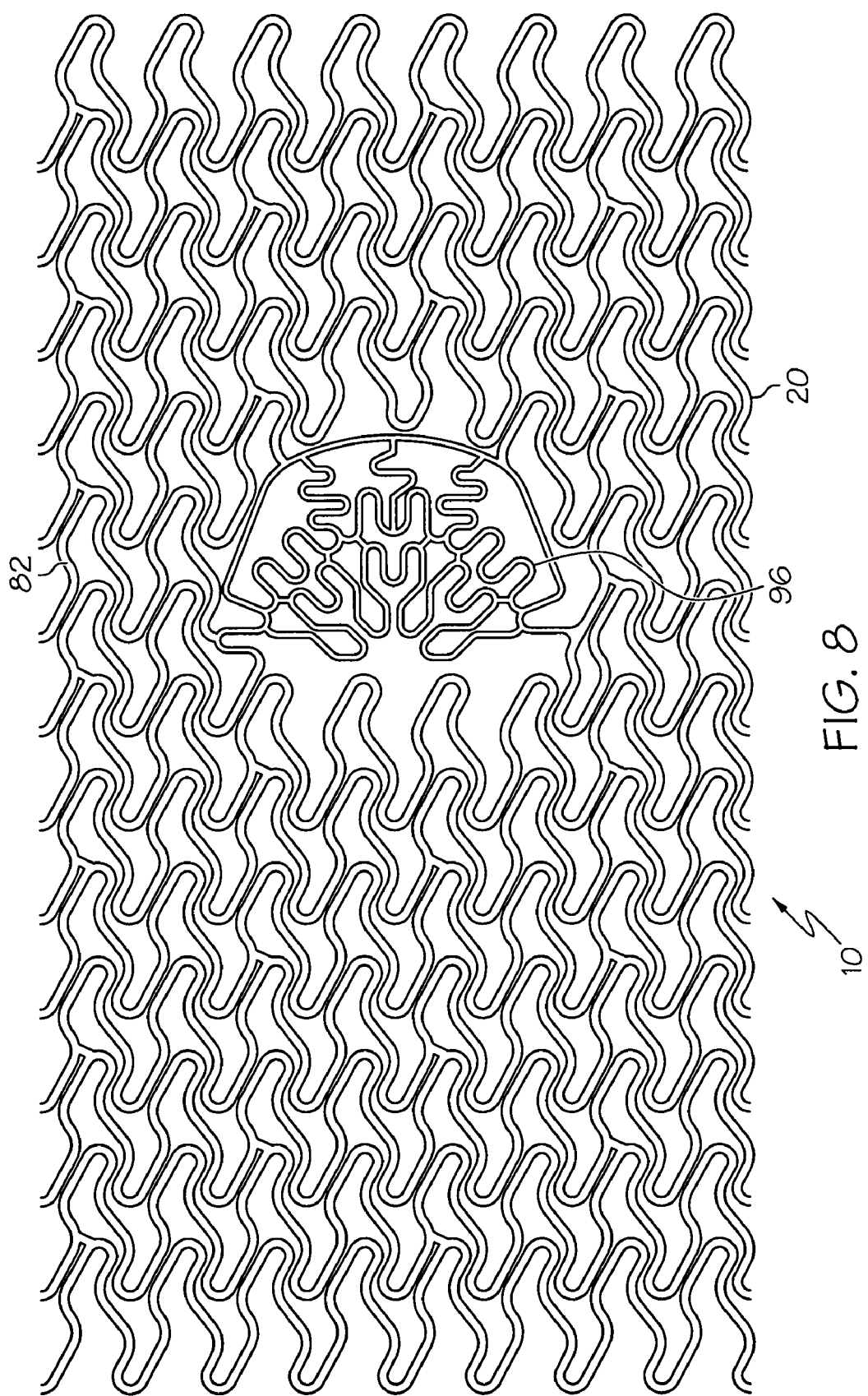
FIG. 8 shows a flat pattern for another embodiment of a stent.

FIG. 8 shows a flat pattern for another embodiment of a stent 10. The stent 10 comprises a plurality of serpentine bands 20 as described herein, for example with respect to FIG. 1. The stent 10 further comprises a partial side branch structure 96 and at least one partial serpentine band 82. A partial serpentine band 82 does not extend about the entire circumference of the stent 10, and generally connects with the partial side branch structure 96.

Stent structure may be expanded into a side branch vessel using any suitable method. In some embodiments, a balloon having a second expandable portion, for example as described in US Patent Application Publication No. 20050060027, may be used to expand either or both of the second portion 78 (see FIG. 6) and the partial side branch structure 96. Self-expanding embodiments are also desirable in that they will automatically expand into the side branch vessel.

The invention is further directed to methods of delivering stents 10 as described herein to a deployment site, and to expanding the stent structure within a main branch vessel and into a side branch vessel, as would be understood by a person of ordinary skill in the art.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A stent having a proximal end and a distal end, the stent comprising:
    a tubular body defined by a plurality of serpentine bands and connectors, adjacent serpentine bands connected by at least one connector;
    each serpentine band comprising a plurality of interconnected proximal turns and distal turns, each proximal turn being longitudinally and circumferentially offset from each distal turn, every proximal turn connected to a first distal turn by a first strut and to a second distal turn by a second strut, each first strut having a shape that is different than that of each second strut, each first strut and each second strut having a peak and a valley, the peak of each strut being closer to the connected distal turn than to the connected proximal turn, the valley of each strut being closer to the connected proximal turn than to the connected distal turn, all peaks being substantially aligned along a first stent circumference, all valleys being substantially aligned along a second stent circumference, the first stent circumference offset from the second stent circumference;
    wherein a connector attaches at one end to a distal turn of one serpentine band and at another end to a location on a second strut of an adjacent serpentine band, said location spaced away from a turn.

2. The stent of claim 1, wherein the peak and the valley of each strut are oriented in opposite directions.

3. The stent of claim 1, wherein the struts of a first serpentine band and the struts of a second serpentine band overlap about a common stent circumference.

4. The stent of claim 3, wherein the distal turns of the first serpentine band are located distal to the common stent circumference, and the proximal turns of the second serpentine band are located proximal to the common stent circumference.

5. The stent of claim 1, wherein said connector attached between said distal turn of one serpentine band and said location on a second strut of said adjacent serpentine band comprises a length that is less than a distance across said distal turn.

6. The stent of claim 1, wherein the distance between the peak and the valley of a first strut is greater than the distance between the peak and the valley of a second strut.

7. The stent of claim 1, wherein each strut comprises a proximal end and a distal end, the distal end of each first strut offset from the proximal end in a first circumferential direction, the distal end of each second strut offset from the proximal end in a second circumferential direction that is different from the first circumferential direction.

8. The stent of claim 1, wherein each first strut comprises a plurality of parallel straight portions.

9. The stent of claim 8, wherein each second strut comprises a plurality of parallel straight portions.

10. The stent of claim 1, wherein each serpentine band comprises a plurality of strut pairs, each strut pair comprising a first strut and a second strut connected by a turn, wherein a strut pair included in a first serpentine band is nested within a strut pair included in a second serpentine band.

11. The stent of claim 1, wherein a first serpentine band is overlapped by a second serpentine band along the length of the stent, the first serpentine band having a total length as measured along the length of the stent, the first serpentine band having an overlapped length as measured along the length of the stent, the overlapped length being at least 25% of the total length.

12. The stent of claim 11, the overlapped length being at least 35% of the total length.

13. The stent of claim 1, wherein the stent is expandable from a delivery diameter to an expanded diameter, the expanded diameter being at least 4 times the delivery diameter.

14. The stent of claim 13, the expanded diameter being at least 4.5 times the delivery diameter, the diameters comprising outer stent diameters.

15. The stent of claim 1, wherein a connector attaches between a distal turn of one serpentine band and a valley of a second strut of an adjacent serpentine band.

16. A stent having a proximal end and a distal end, the stent comprising:
- a tubular body defined by a plurality of serpentine bands;
- each serpentine band comprising a plurality of interconnected proximal turns and distal turns, each proximal turn being longitudinally and circumferentially offset from each distal turn, every proximal turn connected to a first distal turn by a first strut and to a second distal turn by a second strut, each first strut defining a curvilinear path different than that of each second strut, each first strut comprising a plurality of parallel straight portions, each second strut comprising a plurality of parallel straight portions, each first strut and each second strut having a peak and a valley, the peak of each strut being closer to the connected distal turn than to the connected proximal turn, the valley of each strut being closer to the connected proximal turn than to the connected distal turn, all peaks being substantially aligned along a first stent circumference, all valleys being substantially aligned along a second stent circumference,
- wherein the straight portions of the first struts are parallel to the straight portions of the second struts and nonparallel to a stent longitudinal axis, and a first serpentine band overlaps a second serpentine band; and wherein a connector attaches at one end to a distal turn of one serpentine band and at another end to a location on a second strut of an adjacent serpentine band, said location spaced away from a turn such that a common stent circumference intersects struts of the first serpentine band and struts of the second serpentine band.

17. A stent having a proximal end and a distal end, the stent comprising:
- a tubular body defined by a plurality of serpentine bands and connectors, adjacent serpentine bands connected by at least one connector;
- each serpentine band comprising a plurality of interconnected proximal turns and distal turns, each proximal turn being longitudinally and circumferentially offset from each distal turn, every proximal turn connected to a first distal turn by a first strut and to a second distal turn by a second strut, each first strut having a shape that is different than that of each second strut, each first strut and each second strut having a peak and a valley, the peak of each strut being closer to the connected distal turn than to the connected proximal turn, the valley of each strut being closer to the connected proximal turn than to the connected distal turn, all peaks being substantially aligned along a first stent circumference, all valleys being substantially aligned along a second stent circumference, the first stent circumference offset from the second stent circumference; and
- a partial side branch structure comprising at least two outwardly deployable petal structures, said petal structures partially bounding a side branch opening, each petal structure defining a petal axis, said petal axes intersecting at a side branch centerpoint;
- wherein a first serpentine band overlaps a second serpentine band such that a common stent circumference intersects struts of the first serpentine band and struts of the second serpentine band; and wherein a connector attaches at one end to a distal turn of one serpentine band and at another end to a location on a second strut of an adjacent serpentine band, said location spaced away from a turn.

18. The stent of claim 17, wherein the stent may be expanded such that the outwardly deployable petal structures support a vessel bifurcation carina and at least one serpentine band supports a vessel bifurcation contralateral ostial wall.

19. A stent having a longitudinal axis, the stent comprising:
- a tubular body, the tubular body defined by a plurality of circumferential bands connected by connectors, each circumferential band defining a central axis that is collinear with said longitudinal axis;
- each circumferential band comprising of a plurality of interconnected proximal turns and distal turns, each distal turn being longitudinally and circumferentially offset from each proximal turn, every distal turn connected to a first proximal turn by a first strut and to a second proximal turn by a second strut, each first strut having a shape that is different than that of each second strut, each first strut and each second strut having a first bend and a second bend, each first bend of the strut being closer longitudinally along the path to the distal turn which the strut connects than to the proximal turn which the strut connects, each second bend being longitudinally closer along the path to the proximal turn which the strut connects than to the distal turn which the strut connects, all first bends being substantially aligned along a first circumferential axis, all second bends being substantially aligned along a second circumferential axis, the first circumferential axis offset from the second circumferential axis;
- at least one connector being attached at one end to a distal turn of one circumferential band and at another end to a second bend of an adjacent circumferential band.

* * * * *